United States Patent
Kim

(10) Patent No.: US 9,978,959 B2
(45) Date of Patent: May 22, 2018

(54) ORGANOMETALLIC COMPOUND AND ORGANIC LIGHT-EMITTING DIODE INCLUDING THE SAME

(71) Applicant: Samsung Display Co., Ltd., Yongin, Gyeonggi-Do (KR)

(72) Inventor: Myoung-Ki Kim, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 704 days.

(21) Appl. No.: 14/199,533

(22) Filed: Mar. 6, 2014

(65) Prior Publication Data

US 2014/0326964 A1 Nov. 6, 2014

(30) Foreign Application Priority Data

May 2, 2013 (KR) ........................ 10-2013-0049605

(51) Int. Cl.

| | |
|---|---|
| *H01L 51/54* | (2006.01) |
| *C09K 11/06* | (2006.01) |
| *H01L 51/00* | (2006.01) |
| *C07F 15/00* | (2006.01) |
| *H01L 51/50* | (2006.01) |

(52) U.S. Cl.
CPC ...... *H01L 51/0085* (2013.01); *C07F 15/0033* (2013.01); *C09K 11/06* (2013.01); *H01L 51/009* (2013.01); *C09K 2211/1007* (2013.01); *C09K 2211/1029* (2013.01); *C09K 2211/185* (2013.01); *H01L 51/0037* (2013.01); *H01L 51/0042* (2013.01); *H01L 51/5016* (2013.01); *H01L 2251/308* (2013.01)

(58) Field of Classification Search
None
See application file for complete search history.

(56) References Cited

U.S. PATENT DOCUMENTS

| | | | |
|---|---|---|---|
| 2006/0093852 A1* | 5/2006 | Marsitzky et al. .... | C08G 61/02 428/690 |
| 2007/0190358 A1 | 8/2007 | Byun et al. | |
| 2010/0044688 A1 | 2/2010 | Wolleb et al. | |
| 2011/0121279 A1 | 5/2011 | Baranoff et al. | |

FOREIGN PATENT DOCUMENTS

| | | |
|---|---|---|
| JP | 2006-316162 A * | 11/2006 |
| KR | 10-0729739 B1 | 6/2007 |
| KR | 10-2007-0081406 A | 8/2007 |
| KR | 10-2009-0109591 A | 10/2009 |
| KR | 10-2011-0031387 A | 3/2011 |

OTHER PUBLICATIONS

Machine translation of JP 2006-316162 (Nov. 2006).*
Andreiadis et al., "Phosphorescent Binuclear Iridium Complexes . . . Theoretical Study", Inorganic Chemistry, vol. 50, pp. 8197-8206 (Aug. 10, 2011).*
Li et al., "Synthesis and optoelectronic properties of a heterobimetallic Pt(II)-Ir(III) complex . . . in white PLEDs", Dalton Transactions, vol. 41, pp. 2972-2978 (Jan. 25, 2012).*
Wang et al., "White emission from dinuclear cyclometalated platinum(II) complex in single-emitting layer PLEDs", Tetrahedron, vol. 67 (2011), pp. 2118-2124 (available online Jan. 20, 2011).*
Yu et al., "Synthesis and optoelectronic properties of a novel dinuclear cyclometalated platinum(II) complex . . . WPLEDs", Tetrahedron, vol. 70 (2014), pp. 1246-1251 (available online Dec. 31, 2013).*

* cited by examiner

*Primary Examiner* — Marie R. Yamnitzky
(74) *Attorney, Agent, or Firm* — Lee & Morse, P.C.

(57) ABSTRACT

An organometallic compound, an organic light-emitting device including the same, and a method of manufacturing organic light-emitting device, the organometallic compound being represented by Formula 1, below:

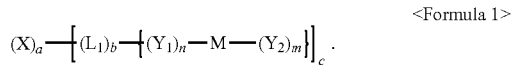

17 Claims, 2 Drawing Sheets

ORGANOMETALLIC COMPOUND AND ORGANIC LIGHT-EMITTING DIODE INCLUDING THE SAME

CROSS-REFERENCE TO RELATED APPLICATION

Korean Patent Application No. 10-2013-0049605, filed on May 2, 2013, in the Korean Intellectual Property Office, and entitled: "Organometallic Compound and Organic Light-Emitting Diode Comprising the Same," is incorporated by reference herein in its entirety.

BACKGROUND

1. Field

Embodiments relate to an organometallic compound and an organic light-emitting device including the organometallic same.

2. Description of the Related Art

Organic light-emitting devices (OLEDs), which are self-emitting devices, have advantages such as wide viewing angles, excellent contrast, quick response, high brightness, excellent driving voltage characteristics, and can provide multicolored images.

An OLED may have a structure including a substrate, and an anode, a hole transport layer (HTL), an emission layer (EML), an electron transport layer (ETL), and a cathode which are sequentially stacked on the substrate. In this regard, the HTL, the EML, and the ETL may be organic thin films formed of organic compounds.

An operating principle of an OLED having the above-described structure may be as follows.

When a voltage is applied between the anode and the cathode, holes injected from the anode may move to the EML via the HTL, and electrons injected from the cathode may move to the EML via the ETL. The holes and electrons may recombine in the EML to generate excitons. When the excitons drop from an excited state to a ground state, light may be emitted.

SUMMARY

Embodiments are directed to an organometallic compound and an organic light-emitting device including the organometallic same.

The embodiments may be realized by providing an organometallic compound represented by Formula 1, below:

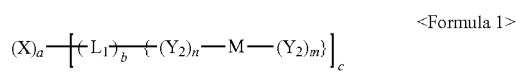

<Formula 1> wherein, in Formula 1, X is selected from a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group; a is an integer of 1 to 5, wherein, when a is 2 or greater, X are identical to or different from each other; $L_1$ is selected from —O—, —S—, or a substituted or unsubstituted alkylene group; b is an integer of 0 to 5, wherein $Y_1$ or $Y_2$ is bound to X when b is 0, $L_1$ is bound to $Y_1$ or $Y_2$ and to X when b is 1 or greater, and $L_1$ are identical to or different from each other when b is 2 or greater; M is a transition metal having an atomic weight of 40 or greater; $Y_1$ is a first ligand selected from a monodentate organic ligand, a bidentate organic ligand, a tridentate organic ligand, or a tetradentate organic ligand; n is an integer of 1 to 4; $Y_2$ is a second ligand represented by Formula 2, below; m is an integer of 1 to 3; c is an integer of 2 to 5, and moieties represented by

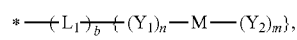

in which * is a binding site to X, are identical to or different from each other;

<Formula 2>

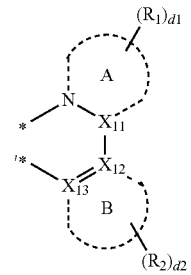

wherein, in Formula 2, $X_{11}$ to $X_{13}$ are each independently a carbon atom (C) or a nitrogen atom (N); ring A is a $C_2$-$C_{60}$ heteroaromatic group including at least one nitrogen atom as a ring member; ring B is selected from a $C_4$-$C_{20}$ alicyclic group, a $C_2$-$C_{20}$ heteroalicyclic group, a $C_6$-$C_{20}$ aromatic group, or a $C_2$-$C_{20}$ heteroaromatic group; $R_1$ and $R_2$ are each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group; d1 is an integer of 1 to 8, wherein, when d1 is 2 or greater, $R_1$ are identical to or different from each other; d2 is an integer of 1 to 8, wherein, when d2 is 2 or greater, $R_2$ are identical to or different from each other; and * and *' in Formula 2 indicate binding sites to M.

X may be selected from a cyclopropane, a cyclobutane, a cyclopentane, a cyclohexane, a cycloheptane, a cyclooctane, a cyclopentene, a cyclopentadiene, a cyclohexadiene, a cycloheptadiene, a bicyclo-heptane, a bicyclo-octane, a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, and a chrysene; and a cyclopropane, a cyclobutane, a cyclopentane, a cyclohexane, a cycloheptane, a cyclooctane, a cyclopentene, a cyclopentadiene, a cyclohexadiene, a cycloheptadiene, a bicyclo-heptane, a bicyclo-octane, a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, and a chrysene, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{30}$ cycloalkyl group, a $C_3$-$C_{30}$ cycloalkenyl group, a $C_3$-$C_{30}$ heterocycloalkyl group, a $C_3$-$C_{30}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$), in which $Q_{11}$ to $Q_{15}$ are each independently, a hydrogen atom, a $C_1$-$C_{10}$ alkyl group, a $C_6$-$C_{20}$ aryl group, or a $C_2$-$C_{20}$ heteroaryl group.

X may be selected from a benzene, a naphthalene, and an anthracene; and a benzene, a naphthalene, and an anthracene, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group; a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

a may be 1 or 2.

X may be a phenylene group, and a may be 1 or 2.

$L_1$ may be selected from —O—; —S—; a $C_1$-$C_{10}$ alkylene group; and a $C_1$-$C_{10}$ alkylene group substituted with at least one of a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkoxy group, a phenyl group, a naphthyl group, an anthryl group, a dimethylfluorenyl group, a phenylcarbazolyl group, a pyridinyl group, a pyrimidinyl group, a pyrazinyl group, and a triazinyl group.

b may be 1 or 2.

b may be 1 or greater, and $L_1$ may be bound to $Y_1$ and X.

In Formula 1, b may be 1 or greater, and the moiety represented by $(L_1)_b$ may be represented by Formula 3, below:

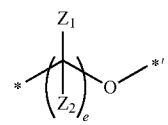

<Formula 3> wherein, in Formula 3, * is a binding site to X; *' is a binding site to $Y_1$ or $Y_2$; $Z_1$ and $Z_2$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkoxy group, a phenyl group, a naphthyl group, an anthryl group, a dimethylfluorenyl group, a phenylcarbazolyl group, a pyridinyl group, a pyrimidinyl group, a pyrazinyl group, and a triazinyl group; and e may be an integer of 1 to 3.

M may be selected from iridium (Ir), platinum (Pt), osmium (Os), and ruthenium (Ru).

The first ligand may be at least one of the groups represented by Formulae 4 to 12, below:

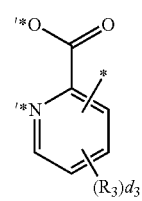

<Formula 4>

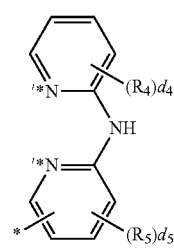

<Formula 5>

<Formula 6>

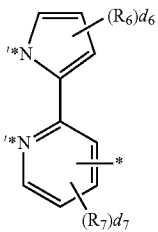

<Formula 7>

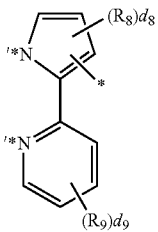

<Formula 8>

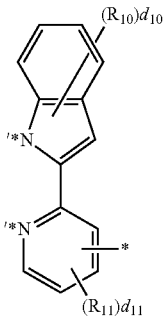

<Formula 9>

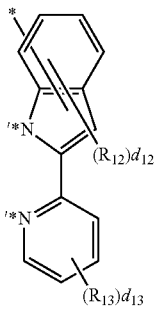

<Formula 10>

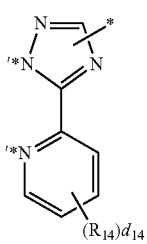

<Formula 11>

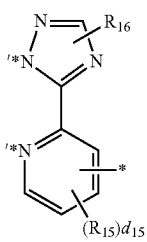

<Formula 12>

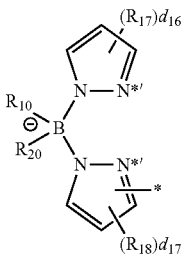

wherein, in Formulae 4 to 12, * is a binding site to $L_1$ or X if $L_1$ is not present; *' is a binding site to M; $R_3$ to $R_{20}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group; and $d_3$ to $d_{17}$ may be each independently an integer of 1 to 3.

In Formula 2, the ring A may be pyridine, and the ring B may be benzene.

In Formula 2, $R_1$ and $R_2$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group; a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

In Formula 1, a moiety represented by

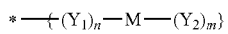

may be a moiety represented by Formula 13 below:

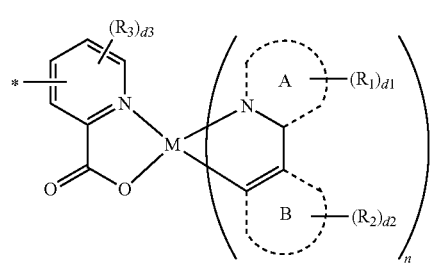

<Formula 13> wherein, in Formula 13 *, is a binding site to $L_1$ or X if $L_1$ is not present; ring A may be selected from a pyridine, a pyrimidine, a pyrazine, a triazine, a quinoline, and an isoquinoline; ring B may be selected from a benzene, a naphthalene, a pyrazole, a triazole, a pyridine, a pyrimidine, a pyrazine, a triazine, a quinoline, and an isoquinoline; $R_1$ to $R_3$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group; a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; and d1 to d3 may be each independently an integer of 1 to 3.

c may be 2 or 3.

The organometallic compound represented by Formula 1 may be one of Compounds 1 to 3 below:

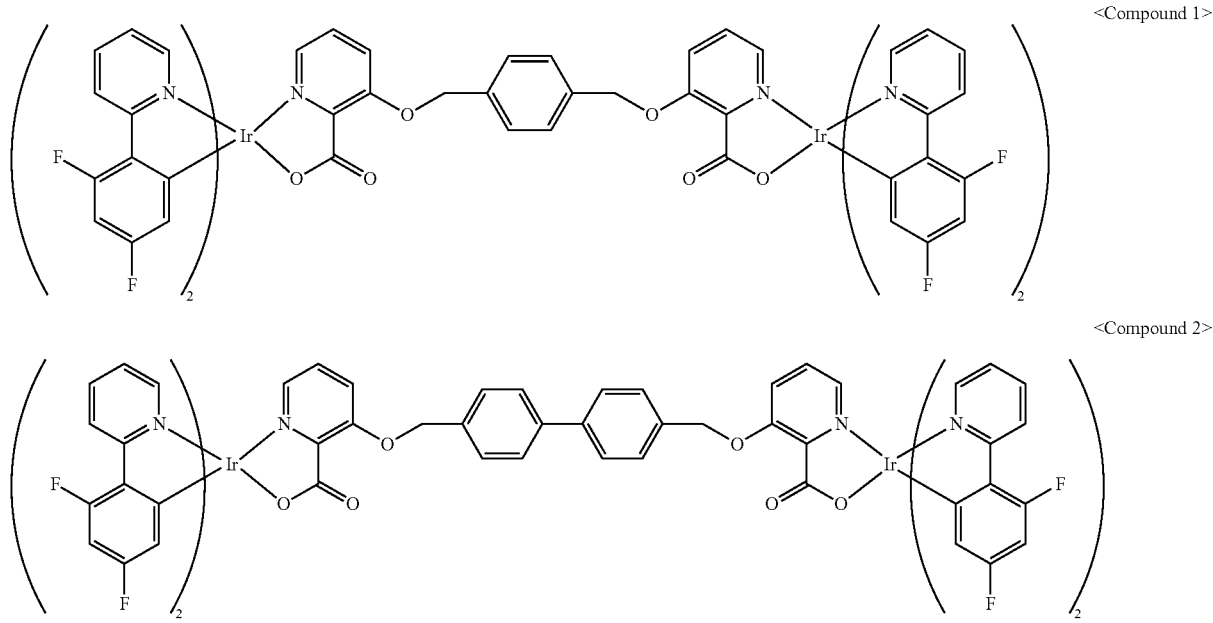

<Compound 1>

<Compound 2>

-continued

<Compound 3>

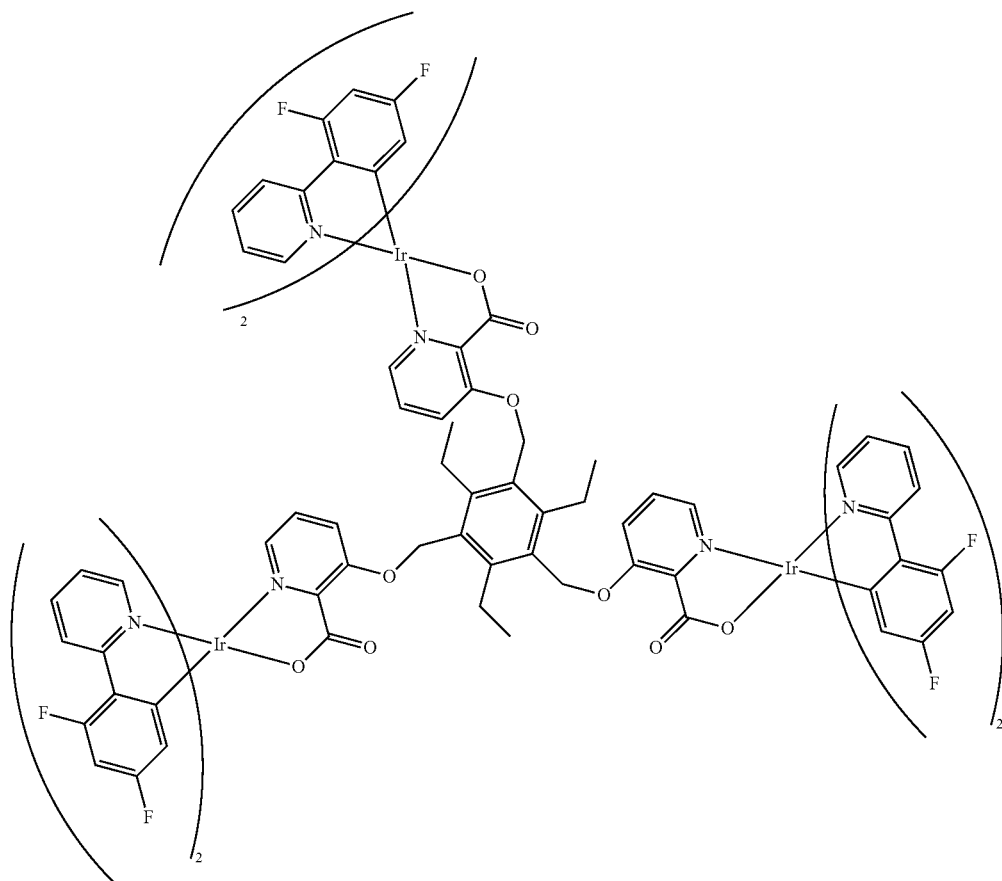

The embodiments may be realized by providing an organic light-emitting device including a substrate; a first electrode; a second electrode disposed opposite to the first electrode; and an organic layer disposed between the first electrode and the second electrode and including an emission layer, the organic layer including the organometallic compound according to an embodiment.

The organic layer may include a hole transport region between the first electrode and the emission layer, the hole transport region including at least one of a hole injection layer, a hole transport layer, a functional layer having a hole injection capability and a hole transport capability, a buffer layer, and an electron blocking layer, and an electron transport region between the emission layer and the second electrode, the electron transport region including at least one selected from a hole blocking layer, an electron transport layer, and an electron injection layer.

The emission layer may include a host and a phosphorescent dopant, the phosphorescent dopant including the organometallic compound.

The embodiments may be realized by providing a method of manufacturing an organic light-emitting device, the method including forming a first electrode on a substrate; forming an organic layer on the first electrode such that the organic layer includes an emission layer and the organometallic compound according to an embodiment; and forming a second electrode on the organic layer, wherein the forming the organic layer includes depositing the organometallic compound on a selected substrate; or applying a mixture of the organometallic compound and a solvent onto a selected substrate, and removing part of the solvent from the mixture applied onto the selected substrate.

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
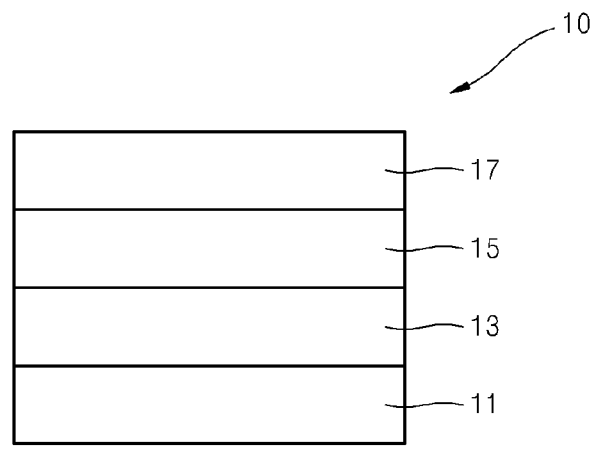
FIG. 1 schematically illustrates the structure of an organic light-emitting device according to an embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

An embodiment may provide an organometallic compound by Formula 1, below.

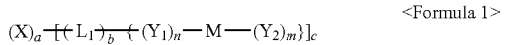

<Formula 1>

In Formula 1, X may be selected from a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, and a substituted or unsubstituted $C_2$-$C_{20}$ heteroaromatic group.

For example, X in Formula 1 above may be selected from:
a $C_4$-$C_{20}$ alicyclic group, a $C_2$-$C_{20}$ heteroalicyclic group, a $C_6$-$C_{20}$ aromatic group, and a $C_2$-$C_{20}$ heteroaromatic group; and
a $C_4$-$C_{20}$ alicyclic group, a $C_2$-$C_{20}$ heteroalicyclic group, a $C_6$-$C_{20}$ aromatic group, and a $C_2$-$C_{20}$ heteroaromatic group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$) (in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group).

In an implementation, X in Formula 1 may be selected from:
a cyclopropane, a cyclobutane, a cyclopentane, a cyclohexane, a cycloheptane, a cyclooctane, a cyclopentene, a cyclopentadiene, a cyclohexadiene, a cycloheptadiene, a bicyclo-heptane, a bicyclo-octane, a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, and a chrysene; and
a cyclopropane, a cyclobutane, a cyclopentane, a cyclohexane, a cycloheptane, a cyclooctane, a cyclopentene, a cyclopentadiene, a cyclohexadiene, a cycloheptadiene, a bicyclo-heptane, a bicyclo-octane, a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, and a chrysene, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{30}$ cycloalkyl group, a $C_3$-$C_{30}$ cycloalkenyl group, a $C_3$-$C_{30}$ heterocycloalkyl group, a $C_3$-$C_{30}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (in which $Q_{11}$ to $Q_{15}$ are each independently a hydrogen atom, a $C_1$-$C_{10}$ alkyl group, a $C_6$-$C_{20}$ aryl group, or a $C_2$-$C_{20}$ heteroaryl group).

In an implementation, X in Formula 1 above may be selected from:
i) a benzene, a naphthalene, and an anthracene; and
ii) a benzene, a naphthalene, and an anthracene, each substituted with at least one selected from
a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group;

a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

In Formula 1 above, a, which indicates the number of Xs, may be an integer of 1 to 5. When a is 2 or greater, a plurality of Xs may be identical to or different from each other.

For example, a in Formula 1 above may be an integer of 1 or 2.

For example, in Formula 1 above, X may be a phenylene group, and a may be an integer of 1 or 2.

In Formula 1, $L_1$ may be selected from —O—, —S—, and a substituted or unsubstituted $C_1$-$C_{10}$ alkylene group.

For example, $L_1$ in Formula 1 above may be selected from —O—; —S—; $C_1$-$C_{10}$ alkylene group; and a $C_1$-$C_{10}$ alkylene group substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{30}$ cycloalkyl group, a $C_3$-$C_{30}$ cycloalkenyl group, a $C_3$-$C_{30}$ heterocycloalkyl group, a $C_3$-$C_{30}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (in which $Q_{11}$ to $Q_{15}$ are each independently a hydrogen atom, a $C_1$-$C_{10}$ alkyl group, a $C_6$-$C_{20}$ aryl group, or a $C_2$-$C_{20}$ heteroaryl group).

In an implementation, $L_1$ in Formula 1 may be selected from —O—; —S—; $C_1$-$C_{10}$ alkylene group; and a $C_1$-$C_{10}$ alkylene group substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkoxy group, a phenyl group, a naphthyl group, an anthryl group, a dimethylfluorenyl group, a phenylcarbazolyl group, a pyridinyl group, a pyrimidinyl group, a pyrazinyl group, and a triazinyl group.

In an implementation, $L_1$ in Formula 1 above may be selected from —O—; —S—; a methylene, an ethylene, a propylene, a n-butylene, an isobutylene, a sec-butylene, a tert-butylene, a n-pentylene, an isopentylene, a sec-pentylene, a tert-pentylene, a n-hexylene, an isohexylene, a sec-hexylene, a tert-hexylene; and a methylene, an ethylene, a propylene, a n-butylene, an isobutylene, a sec-butylene, a tert-butylene, a n-pentylene, an isopentylene, a sec-pentylene, a tert-pentylene, a n-hexylene, an isohexylene, a sec-hexylene, and a tert-hexylene, each substituted with at least one selected from a deuterium atom, —F, a hydroxyl group, a cyano group, a nitro group, and an amino group.

In Formula 1, b, which indicates the number of $L_1$s, may be an integer of 0 to 5. When b is 0, $Y_1$ or $Y_2$ may be bound to X. When b is 1 or greater, $L_1$ may be bound to $Y_1$ or $Y_2$, and to X. When b is 2 or greater, a plurality of $L_1$s may be identical to or different from each other.

For example, b in Formula 1 above may be 1 or 2.

In an implementation, in Formula 1 above, b may be 1 or greater, and $L_1$ may be bound to $Y_1$ and X.

In an implementation, in Formula 1, b may be 1 or 2, and $L_1$ may be bound to $Y_1$ and X.

For example, in Formula 1 above, b may be 1 or greater, and $(L_1)_b$ may be a moiety represented by Formula 3 below.

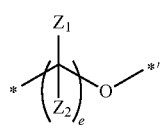

<Formula 3>

In Formula 3 above, * may be a binding site to X; *' may be a binding site to $Y_1$ or $Y_2$; and $Z_1$ and $Z_2$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{30}$ cycloalkyl group, a $C_3$-$C_{30}$ cycloalkenyl group, a $C_3$-$C_{30}$ heterocycloalkyl group, a $C_3$-$C_{30}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, —N($Q_{11}$)($Q_{12}$), and —Si($Q_{13}$)($Q_{14}$)($Q_{15}$) (in which $Q_{11}$ to $Q_{15}$ are each independently a hydrogen atom, a $C_1$-$C_{10}$ alkyl group, a $C_6$-$C_{20}$ aryl group, or a $C_2$-$C_{20}$ heteroaryl group); and e may be an integer of 1 to 3.

For example, $Z_1$ and $Z_2$ in Formula 3 may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkoxy group, a phenyl group, a naphthyl group, an anthryl group, a dimethylfluorenyl group, a phenylcarbazolyl group, a pyridinyl group, a pyrimidinyl group, a pyrazinyl group, and a triazinyl group.

In some embodiments, in Formula 3 above, * may be a binding site to X, *' may be a binding site to $Y_1$ or $Y_2$; and $Z_1$ and $Z_2$ may be each independently selected from a hydrogen atom, a deuterium atom, a halogen atom, a hydroxyl group, a cyano group, and a nitro group; and e may be 1. For example, in Formula 1, X or $L_1$ (when present) may be bound to either $Y_1$ or $Y_2$, and the other of $Y_1$ or $Y_2$ may be a pendant group.

In Formula 1 above, M may be a transition metal having an atomic weight of 40 or greater.

For example, M in Formula 1 above may be selected from iridium (Ir), platinum (Pt), osmium (Os), lead (Pb), rhenium (Re), ruthenium (Ru), or palladium (Pd).

In an implementation, M in Formula 1 above may be selected from iridium (Ir), platinum (Pt), osmium (Os), or ruthenium (Ru).

In another embodiment, M in Formula 1 may be iridium (Ir).

In Formula 1 above, $Y_1$ may be a first ligand selected from a monodentate organic ligand, a bidentate organic ligand, a tridentate organic ligand, and a tetradentate organic ligand.

For example, $Y_1$ in Formula 1 above may be a monodentate organic ligand selected from among an iodide ion, a bromide ion, a chloride ion, a sulfide, a thioxyanate ion, a nitrate ion, an azide ion, a hydroxide ion, water, an isocyanate ion, acetonitrile, a pyridine, ammonia, a cyanide ion, and carbon monoxide.

For example, $Y_1$ in Formula 1 above may be a bidentate organic ligand selected from an oxalate ion, acetylacetonate, 1,2-bis(diphenylphosphino)ethene (dppe), 1,1-bis(diphenylphosphino)methene (dppm), glycinate, ethylenediamine, 2,2'-bipyridine, and 1,10-phenanthroline.

For example, $Y_1$ in Formula 1 above may be a tridentate organic ligand selected from diethylenetriamine (dien), terpyridine, and triazacyclononane.

For example, $Y_1$ in Formula 1 above may be a tetradentate organic ligand selected from heme, triethylenetetramine (trien), tris(2-aminoethyl)amine (tren), and tris(2-diphenylphosphineethyl)amine ($np_3$).

In an implementation, $Y_1$ in Formula 1 above may be selected from groups represented by Formulae 4 to 12, below.

<Formula 4>

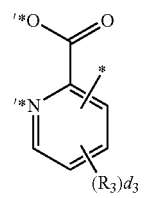

<Formula 5>

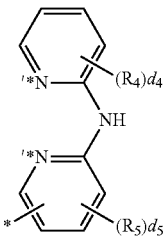

<Formula 6>

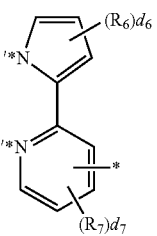

<Formula 7>

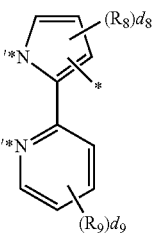

<Formula 8>

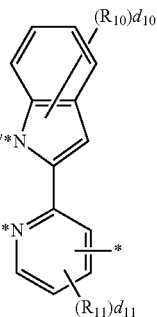

<Formula 9>

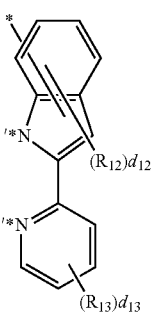

<Formula 10>

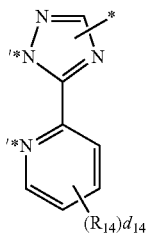

<Formula 11>

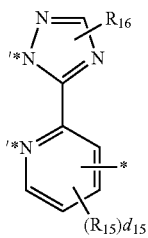

<Formula 12>

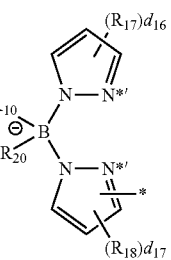

In Formulae 4 to 12, * indicates a binding site to $L_1$ or X, and *' is a binding site of M.

In Formulae 4 to 12, $R_3$ to $R_{20}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$) (in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group).

In Formulae 4 to 12, d3 to d17 may be each independently an integer of 1 to 3.

In an implementation, $Y_1$ in Formula 1 above may be a group represented by Formula 4, below.

<Formula 4>

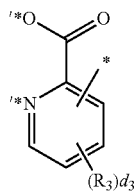

In Formula 4 above, * may be a binding site to $L_1$ or X; and *' may be a binding site to M. In Formula 4, $R_3$ may be selected from:

a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group;

a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, and d3 may be an integer of 1 to 3.

In Formula 1 above, n, which indicates the number of $Y_1$s, may be an integer of 1 to 4.

For example, n in Formula 1 may be 1.

In Formula 1 above, m, which indicates the number of $Y_2$s, may be an integer of 1 to 3.

For example, m in Formula 1 may be an integer of 1 or 2.

In Formula 1 above, c, which indicates the number of moieties represented by $$*-(L_1)_b-(Y_1)_n-M-(Y_2)_m\}$$

(where * is a binding site to X), may be an integer of 2 to 5. For example, c number of the plurality of moieties of $$*-(L_1)_b-(Y_1)_n-M-(Y_2)_m\}$$

may be the same or different.

For example, c in Formula 1 may be an integer of 2 or 3.

In Formula 1 above, $Y_2$ may be a second ligand represented by Formula 2 below.

<Formula 2>

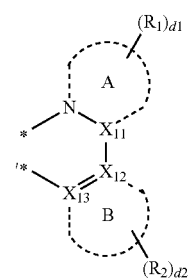

In Formula 2 above, $X_{11}$ to $X_{13}$ may be each independently a carbon atom (C) or a nitrogen atom (N).

For example, in Formula 2, $X_{11}$ may be C, $X_{12}$ may be C, and $X_{13}$ may be C.

In an implementation, in Formula 2, $X_{11}$ may be C, $X_{12}$ may be C, and $X_{13}$ may be N.

In Formula 2 above, the ring A may be a $C_2$-$C_{60}$ heteroaromatic group including at least one nitrogen atom as a ring member.

For example, the ring A in Formula 2 above may be selected from a pyrrole, an imidazole, a pyrazole, a triazole, a thiazole, an oxazole, an isothiazole, an isoxazole, a benzothiazole, a benzoimidazole, a benzoxazole, a pyridine, a pyrazine, a pyrimidine, a pyridazine, an isoindole, an indole, an indazole, a purine, an isoquinoline, a quinoline, a phthalazine, a naphthyridin, a quinoxaline, a quinazoline, a cinnoline, a phenanthridine, an acridine, a phenanthroline, a phenazine, and a phenoxazine.

In an implementation, the ring A of Formula 2 may be selected from a pyridine, a pyrimidine, a pyrazine, a triazine, a quinoline, and an isoquinoline.

In an implementation, the ring A of Formula 2 may be a pyridine.

In Formula 1 above, the ring B may be selected from a $C_4$-$C_{20}$ alicyclic group, a $C_2$-$C_{20}$ heteroalicyclic group, a $C_6$-$C_{20}$ aromatic group, and a $C_2$-$C_{20}$ heteroaromatic group.

For example, the ring B in Formula 2 may be selected from a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, a chrysene, a pyrrole, an imidazole, a pyrazole, a triazole, an isothiazole, an isoxazole, a pyridine, a pyrazine, a pyrimidine, a pyridazine, an isoindole, an indole, an indazole, a purine, an isoquinoline, a quinoline, a phthalazine, a naphthyridin, a quinoxaline, a quinazoline, a cinnoline, a phenanthridine, an acridine, a phenanthroline, a phenazine, a phenoxazine, and a phenoxazine.

In an implementation, the ring B of Formula 2 may be selected from a benzene, a naphthalene, a pyrazole, a triazole, a pyridine, a pyrimidine, a pyrazine, a triazine, a quinoline, and an isoquinoline.

In an implementation, the ring B of Formula 2 may be a benzene.

In an implementation, in Formula 2 above, ring A may be pyridine, ring B may be benzene.

In Formula 2 above, $R_1$ and $R_2$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, $-N(Q_1)(Q_2)$, $-C(=O)(Q_3)$, and $-Si(Q_4)(Q_5)(Q_6)$ (in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group).

For example, $R_1$ and $R_2$ in Formula 2 may be each independently selected from:

a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof; a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group;

a phenyl group, a naphthyl group, an anthryl group, a carbazolyl group, a fluorenyl group, a pyridinyl group, a pyrimidinyl group, a pyrazinyl group and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

In Formula 2 above, d1 indicates the number of $R_1$s, and $R_1$ is a substituent of the ring A in Formula 2. For example, d1 may be an integer of 1 to 8. When d1 is 2 or greater, the two or more $R_1$s may be identical to or different from each other. When $R_1$s are all hydrogen atoms, the ring A of Formula 2 is a unsubstituted ring.

In Formula 2 above, d2 indicates the number of $R_2$s, and $R_2$ is a substituent of the ring B in Formula 2. For example, d2 may be an integer of 1 to 8. When d2 is 2 or greater, the two or more $R_2$s may be identical to or different from each other. When $R_2$s are all hydrogen atoms, the ring B of Formula 2 is a unsubstituted ring.

In Formula 2 above, * and *' may be binding sites to M.

In Formula 1 above, a moiety represented by

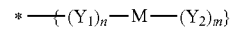

may be a moiety represented by Formula 13 below.

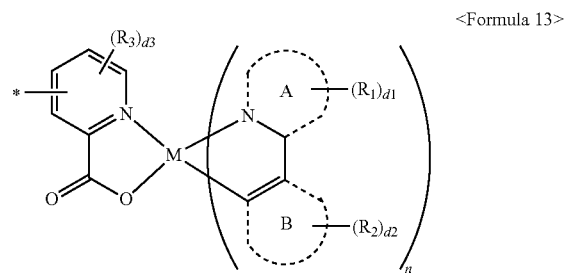

<Formula 13>

In Formula 13 above,

* may be a binding site to $L_1$ or X,

Ring A may be selected from a pyridine, a pyrimidine, a pyrazine, a triazine, a quinoline, and an isoquinoline, Ring B may be selected from a benzene, a naphthalene, a pyrazole, a triazole, a pyridine, a pyrimidine, a pyrazine, a triazine, a quinoline, and an isoquinoline; $R_1$ to $R_3$ may be each independently selected from:

a hydrogen atom, a deuterium atom, a halogen atom, a hydroxyl group, a cyano group, a nitro group, an amino group, an amidino group, a hydrazine, a hydrazone, a carboxylic acid group or a salt thereof, a sulfonic acid group or a salt thereof and a phosphoric acid group or a salt thereof;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group;

a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxyl group, a cyano group, a nitro group, and an amino group;

a phenyl group, a naphthyl group, an anthryl group, a carbazolyl group, a fluorenyl group, a pyridinyl group, a pyrimidinyl group, a pyrazinyl group, and a triazinyl group; and a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, and d1 to d3 may be each independently an integer of 1 to 3.

The organometallic compounds represented by Formula 1 above may be one of Compounds 1 to 3 below.

<Compound 1>

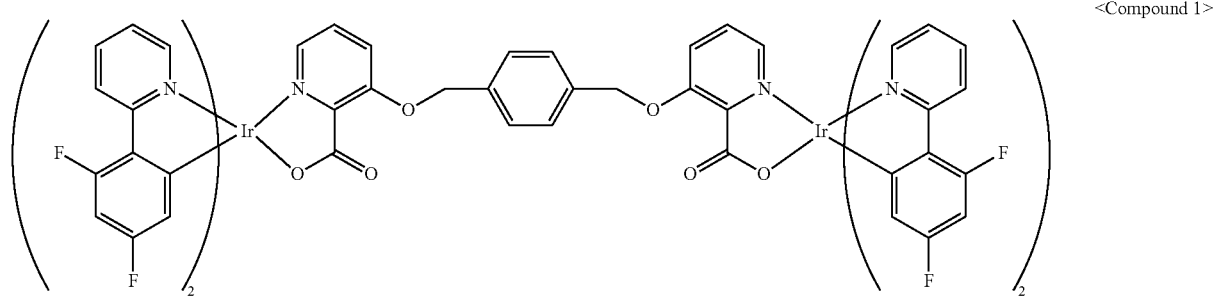

<Compound 2>

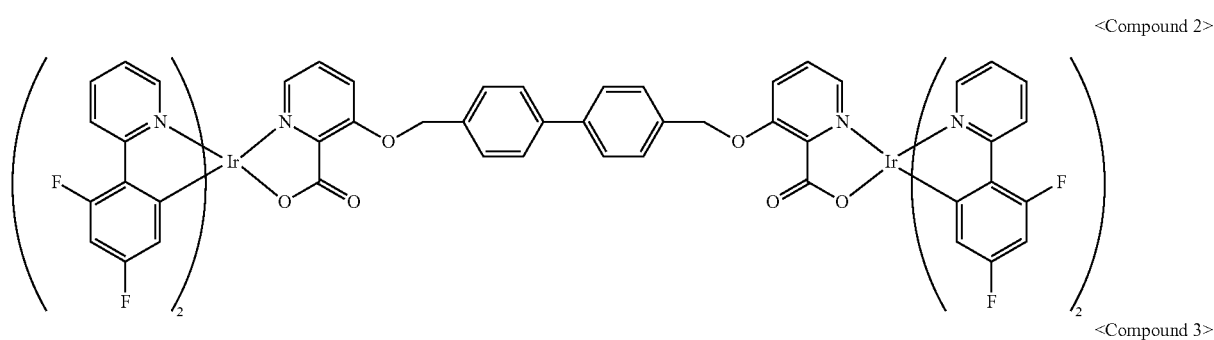

<Compound 3>

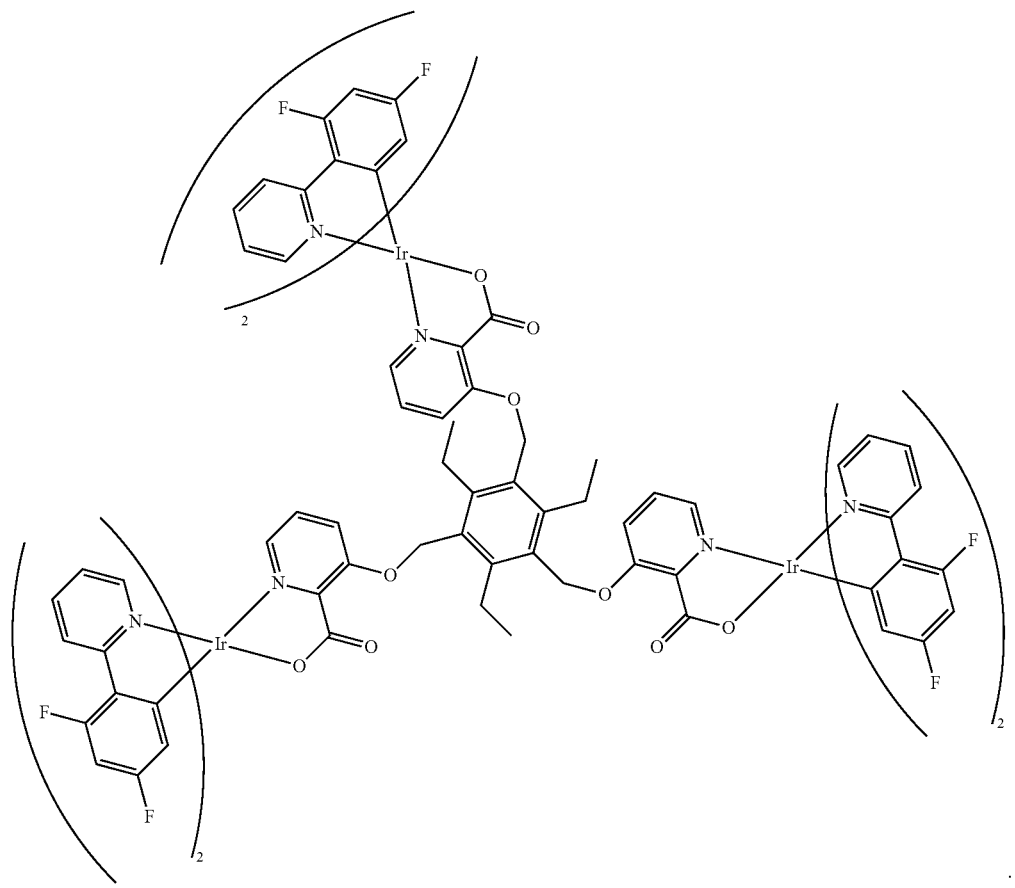

In the organometallic compound of Formula 1 above, c may be an integer of 2 or greater, which indicates the inclusion of at least two transition metal moieties or complexes. Accordingly, the organometallic compound of Formula 1 may have a larger molecular weight and a higher emission efficiency, compared to a compound including only one transition metal moiety or complex. The higher emission efficiency may be attributed to the fact that the organometallic compound of Formula 1 may have a higher purity, compared to a compound using a transition metal complex also bound to a polymer material.

The organometallic compound of Formula 1 above may have a larger molecular weight due to the binding of $L_1$ and $Y_1$, as seen in Formula 1' below. Accordingly, the organometallic compound of Formula 1 above may have a high viscosity, so that an organic layer formed through a solution process may have good quality. Furthermore, the forming of an organic layer via a solution process may be less costly, so that an organic light-emitting device may be economically manufactured.

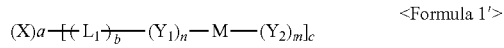
<Formula 1'>

The organometallic compounds represented by Formula 1 above may include —O—, as seen in Formula 3' below, and thus may encounter less steric hindrance, and consequently may be easily synthesized through an $SN^2$ mechanism.

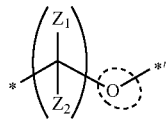
<Formula 3'>

For example, the organometallic compounds represented by Formula 1 above may be a phosphorescent dimer or trimer.

The organometallic compound of Formula 1 above may be synthesized using a suitable organic synthesis. A synthesis method of the organometallic compound of Formula 1 above may correspond with the examples that will be described below.

At least one of the organometallic compounds of Formula 1 may be used between a pair of electrodes of an organic light-emitting device, for example, in an emission layer of an organic light-emitting device.

According to another embodiment, an organic light-emitting device may include a substrate, a first electrode, a second electrode disposed opposite to the first electrode, and an organic layer disposed between the first electrode and the second electrode. The organic layer may include at least one of the organometallic compounds of Formula 1 described above.

The organometallic compound of Formula 1 above may be provided to an organic light-emitting device, e.g., by i) depositing the organometallic compound on a selected substrate of the organic light-emitting device; or by ii) by applying a mixture of the organometallic compound of Formula 1 and a solvent onto a selected substrate and removing part of the solvent from the mixture applied onto the selected substrate.

As used herein, "(for example, the organic layer) including at least one organometallic compound means that "(the organic layer) including one of the organometallic compounds of Formula 1 above, or at least two different organometallic compounds of Formula 1 above".

In an implementation, the organic layer may include only Compound 1. Compound 1 may be in the emission layer of the organic light-emitting device. In an implementation, the organic layer may include Compounds 1 and 2. Compound 1 and Compound 2 may be included in the same layer, e.g., in the emission layer.

The organic layer may include a hole transport region between the first electrode and the emission layer, and that may further include at least one of a hole injection layer, a hole transport layer, a functional layer ("H-functional layer") having both hole injection and hole transport capabilities, a buffer layer, an electron blocking layer, and an electron transport region between the emission layer and the second electrode and that may further include at least one of a hole blocking layer, an electron transport layer, and an electron injection layer.

The term "organic layer" as used herein refers to a single layer and/or a plurality of layers disposed between the first and second electrodes of the organic light-emitting device.

The organic layer may include an emission layer. At least one of the organometallic compounds may be included in the emission layer.

For example, the emission layer may further include a host, and the organometallic compounds represented by Formula 1 in the emission layer may serve as a phosphorescent dopant. Types of the host will be described below.

As described above, an organic light-emitting device including the organometallic compounds represented by Formula 1 above may emit blue light, e.g., a phosphorescent blue light.

FIG. 1 illustrates a schematic sectional view of an organic light-emitting device 10 according to an embodiment. Hereinafter, a structure of an organic light-emitting device according to an embodiment and a method of manufacturing the same will now be described with reference to FIG. 1.

Referring to FIG. 1, the organic light-emitting device 10 may include a substrate 11, a first electrode 13, an organic layer 15, and a second electrode 17.)

The substrate 11 may be a suitable substrate for organic light-emitting devices. In an implementation, the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode or a transmission electrode. Transparent and conductive materials such as ITO, IZO, $SnO_2$, or ZnO may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary depending on the compound that is used to form the HIL, and the desired structure and thermal properties of the HIL to be formed. For example, vacuum deposition may be performed at a temperature of about 100° C. to about 500° C., a pressure of about $10^{-8}$ ton to about $10^{-3}$ ton, and a deposition rate of about 0.01 to about 100 Å/sec.

When the HIL is formed using spin coating, the coating conditions may vary depending on the compound that is used to form the HIL, and the desired structure and thermal properties of the HIL to be formed. For example, the coating rate may be in the range of about 2,000 rpm to about 5,000 rpm, and a temperature at which heat treatment is performed to remove a solvent after coating may be in the range of about 80° C. to about 200° C.

The HIL may be formed of a suitable material for forming a HIL. Non-limiting examples of the material that can be used to form the HIL may include N,N'-diphenyl-N,N'-bis-[4-(phenyl-m-tolyl-amino)-phenyl]-biphenyl-4,4'-diamine, (DNTPD), a phthalocyanine compound such as copper-phthalocyanine, 4,4',4"-tris(3-methylphenylphenylamino) triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS):

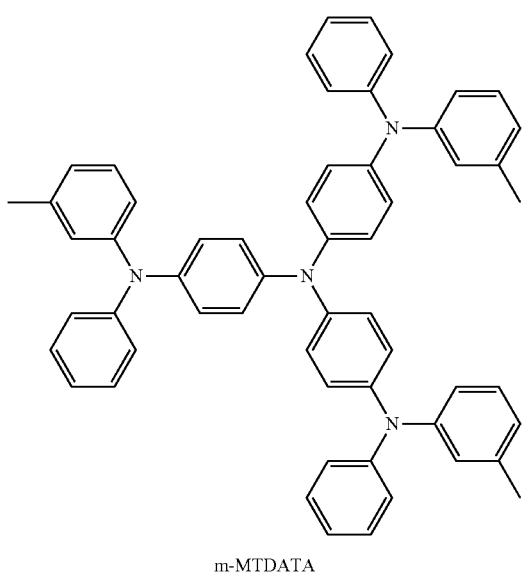

m-MTDATA

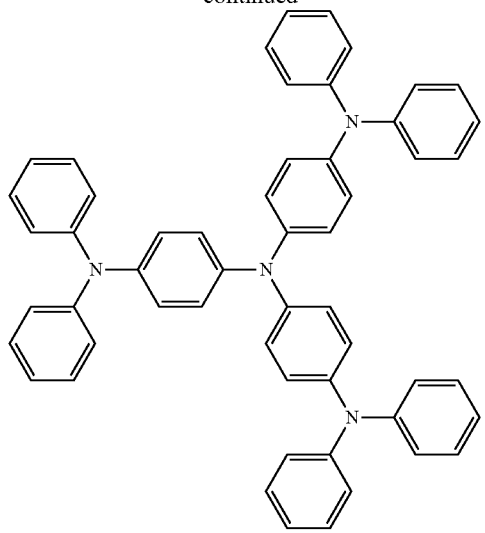

TDATA

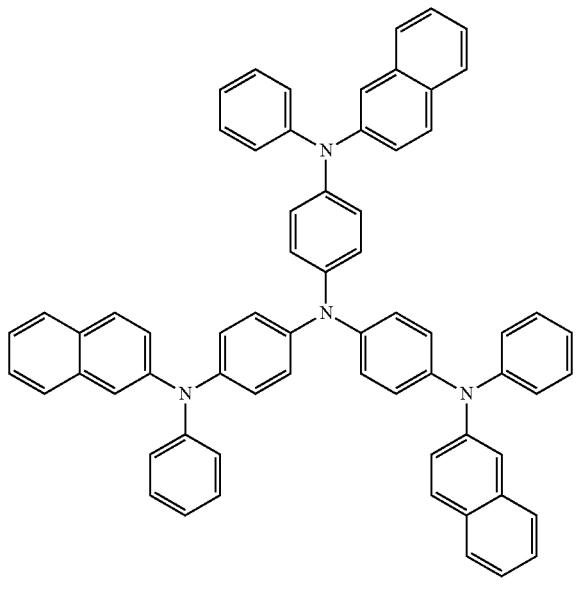

2-TNATA

The thickness of the HIL may be about 100 Å to about 10,000 Å, e.g., about 100 Å to about 1,000 Å. When the thickness of the HIL is within these ranges, the HIL may have good hole injecting ability without a substantial increase in driving voltage.

The HIL may further include a charge-generating material, in addition to a HIL material as listed above, for higher conductivity.

The charge-generating material may be, e.g., a p-dopant. Non-limiting examples of the p-dopant may include quinone derivatives such as tetracyanoquinone dimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

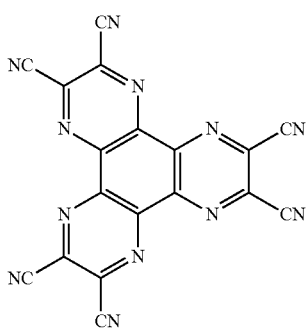
<Compound 100>

When the HIL further include such a charge-generating material, the charge-generating material may be homogeneously dispersed or inhomogeneously or heterogeneously distributed in the HIL layer, but may be present in the HIL layer in any of various forms.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary depending on the material that is used to form the HTL.

Non-limiting examples of suitable hole transport materials may include carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), and N,N'-di(1-naphthyl)-N,N'-diphenylbenzidine) (NPB).

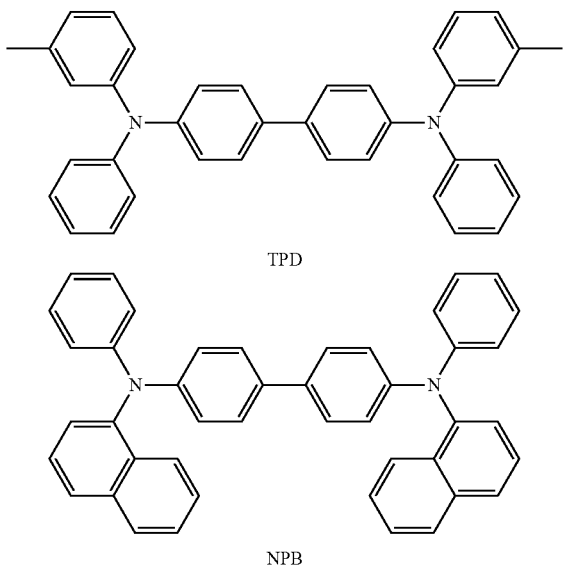

TPD

NPB

The thickness of the HTL may be from about 50 Å to about 2,000 Å, e.g., about 100 Å to about 1,500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 500 Å to about 10,000 Å, e.g., 100 Å to about 1,000 Å. When the thickness of the H-functional layer is within these ranges, the H-functional layer may have good hole injection and transport capabilities without a substantial increase in driving voltage.

At least one of the HIL, HTL, and H-functional layer may further include a charge-generating material for improved layer conductivity, in addition to a suitable hole injecting material, hole transport material, and/or material having both hole injection and hole transport capabilities as described above.

The charge-generating material may be, e.g., a p-dopant. The p-dopant may include one of quinone derivatives, metal oxides, and compounds with a cyano group. Non-limiting examples of the p-dopant may include quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

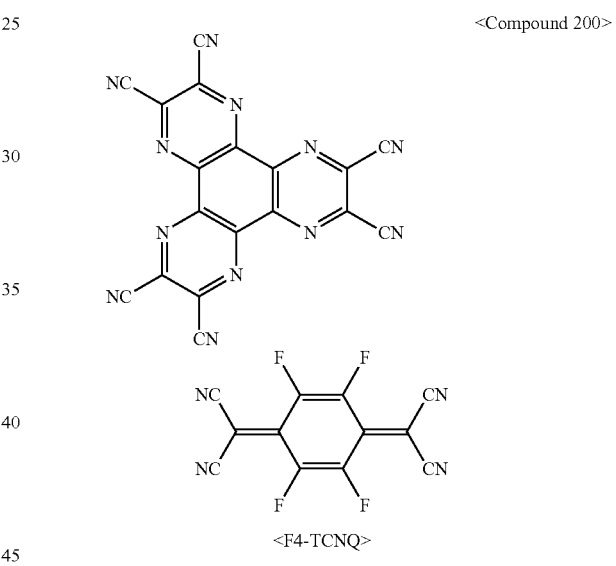
<Compound 200>

<F4-TCNQ>

When the hole injection layer, hole transport layer, or H-functional layer further includes a charge-generating material, the charge-generating material may be homogeneously dispersed or heterogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include a suitable hole injecting material or hole transporting material. In an implementation, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodgett (LB) deposition, or the like. When the EML is foamed using vacuum deposition or spin coating, the deposition and coating conditions may be similar to those for the formation of the HIL, though the conditions for deposition and coating may vary depending on the material that is used to form the EML.

The EML may include at least one of the organometallic compounds of Formula 1.

The organometallic compounds represented by Formula 1 in the EML may serve as a dopant, e.g., a blue phosphorescent dopant. The EML may further include a host, in addition to the organometallic compounds represented by Formula 1.

The host may include a suitable host material. Non-limiting examples of the suitable host material may include Alq₃, 4,4'-N,N'-dicarbazole-biphenyl (CBP), poly(n-vinyl-carbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), mCP, and OXD-7.

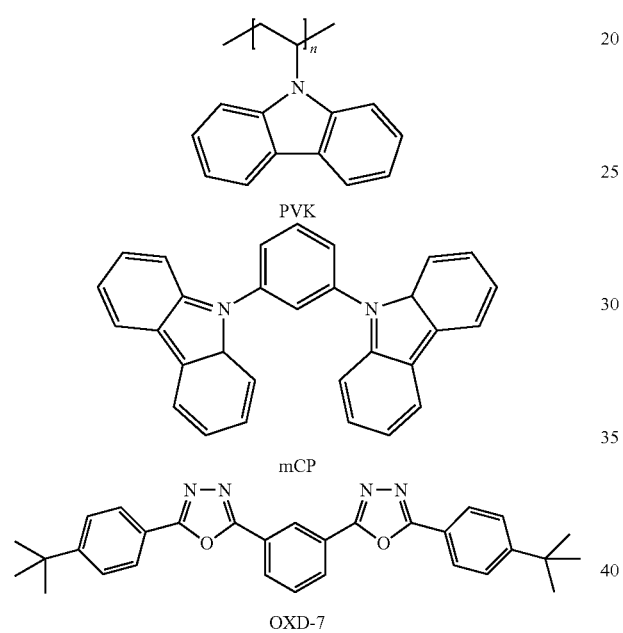

When the EML includes a host and a dopant (e.g., the organometallic compounds represented by Formula 1 above), an amount of the dopant may be from about 0.01 wt % to about 15 wt %, based on a total weight of the EML.

The EML may have a thickness of about 200 Å to about 700 Å. When the thickness of the EML is within this range, the EML may have good light emitting ability without a substantial increase in driving voltage.

Then, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary depending on the compound that is used to form the ETL. A material for forming the ETL may include a suitable material that can stably transport electrons injected from an electron injecting electrode (cathode). Non-limiting examples of materials for forming the ETL may include a quinoline derivative, such as tris(8-quinolinorate)aluminum (Alq3), TAZ, BAlq, beryllium bis(benzoquinolin-10-olate (Bebq₂), 9,10-di(naphthalene-2-yl)anthracene (ADN), Compound 101, Compound 102, and Bphen.

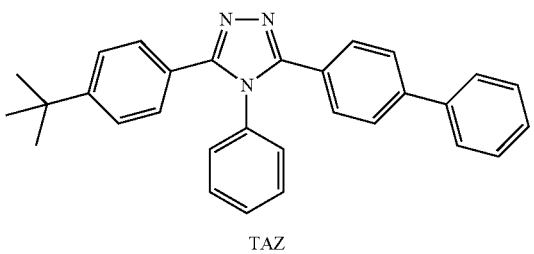

TAZ

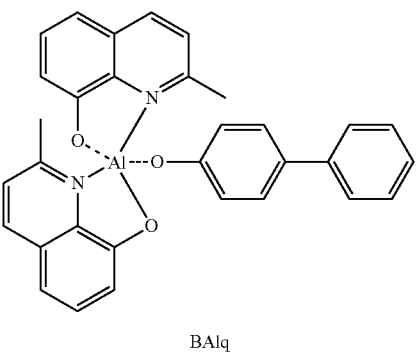

BAlq

<Compound 101>

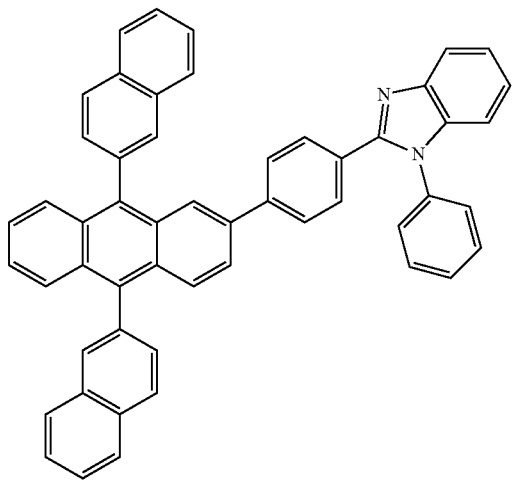

<Compound 102>

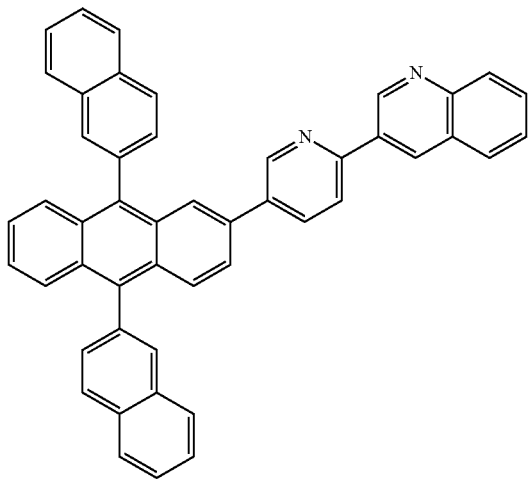

-continued

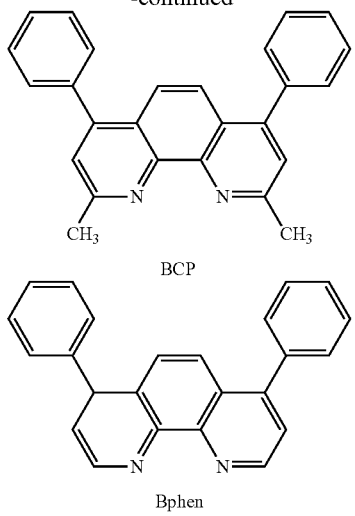

BCP

Bphen

The thickness of the ETL may be from about 100 Å to about 1,000 Å, e.g., about 150 Å to about 500 Å. When the thickness of the ETL is within these ranges, the ETL may have satisfactory electron transporting ability without a substantial increase in driving voltage.

In an implementation, the ETL may further include a metal-containing material, in addition to a suitable electron-transporting organic compound.

The metal-containing compound may include a lithium (Li) complex. Non-limiting examples of the Li complex may include lithium quinolate (Liq) and Compound 203 below:

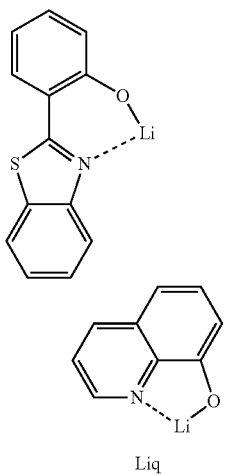

<Compound 203>

Liq

Non-limiting examples of materials for forming the EIL may include LiF, NaCl, CsF, $Li_2O$, and BaO. The deposition and coating conditions for forming the EIL may be similar to those for the formation of the HIL, though the deposition and coating conditions may vary depending on the material that is used to form the EIL.

The thickness of the EIL may be from about 1 Å to about 100 Å, e.g., about 3 Å to about 90 Å. When the thickness of the EIL is within these ranges, the EIL may have satisfactory electron injection ability without a substantial increase in driving voltage.

The second electrode 17 may be disposed on the organic layer 15. The second electrode 17 may be a cathode that is an electron injection electrode. A material for forming the second electrode 17 may include a metal, an alloy, an electro-conductive compound, which have a low work function, or a mixture thereof. In this regard, the second electrode 17 may include, e.g., lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In an implementation, to manufacture a top-emission light-emitting device, the transmission electrode may be formed of indium tin oxide (ITO) or indium zinc oxide (IZO).

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to help reduce and/or prevent diffusion of triplet excitons or holes into the ETL. When the HBL is formed using vacuum deposition or spin coating, the conditions for deposition and coating may be similar to those for the formation of the HIL, although the conditions for deposition and coating may vary depending on the material that is used to form the HBL. A suitable hole-blocking material may be used. Non-limiting examples of hole-blocking materials may include oxadiazole derivatives, triazole derivatives, and phenanthroline derivatives. For example, bathocuproine (BCP) represented by the following formula may be used as a material for forming the HBL.

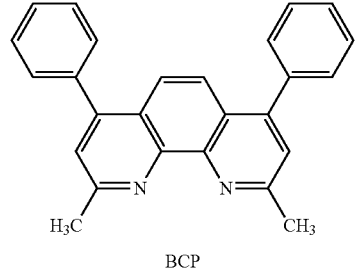 [SMILES: Cc1cc(-c2ccccc2)c2ccc3c(-c4ccccc4)cc(C)nc3c2n1 ; "BCP"]

BCP

The thickness of the HBL may be from about 20 Å to about 1,000 Å, e.g., about 30 Å to about 300 Å. When the thickness of the HBL is within these ranges, the HBL may have improved hole blocking ability without a substantial increase in driving voltage.

At least one of the organometallic compounds of Formula 1 may be used between a pair of electrodes of an organic light-emitting device, e.g., in an emission layer of an organic light-emitting device.

According to another embodiment, a method of manufacturing an organic light-emitting device may include: forming a first electrode on a substrate; forming an organic layer on the first electrode, the organic layer including an emission layer and at least one of the organometallic compounds represented by Formula 1 above; and forming a second electrode on the organic layer. Forming the organic layer may include: i) depositing the at least one of the organometallic compounds on a selected substrate; or ii) applying a mixture of the at least one of the organometallic compounds and a solvent onto a selected substrate, and removing part of the solvent from the mixture applied onto the selected substrate.

The selected substrate refers to an organic layer underlying the organic layer including the organometallic compound of Formula 1, which may be homogeneous or heterogeneous from the organometallic compound-included organic layer. When an organic light-emitting device includes a plurality of organic layers between a first electrode and an emission layer, and the emission layer includes the organometallic compound of Formula 1 above, the selected substrate may be one of the organic layers between the first electrode and the emission layer, most near to the emission layer.

For example, in an organic light-emitting device including a substrate, a first electrode, a hole transport layer, an emission layer, an electron transport layer, and a second electrode that are sequentially stacked upon one another, when the emission layer includes the organometallic compound of Formula 1 above, the selected substrate may be the hole transport layer underlying the emission layer. In another embodiment, when the organic light-emitting device further includes at least one of a hole injection layer, a hole transport layer, a functional layer having both hole injection and hole transport capabilities ("H-functional layer"), a buffer layer, and an electron blocking layer between the first electrode and the emission layer, the selected substrate may be any of these organic layers between the first electrode and the emission layer that is most near to the emission layer.

When the emission layer including the organometallic compounds represented by Formula 1 is formed on a donor substrate which attached a heat transfer film, then the emission layer may be formed by using the donor substrate, and the selected substrate may be the heat transfer film.

The applying of a mixture of the organometallic compound and a solvent onto a selected substrate may include a process involved in a suitable method of manufacturing an organic light-emitting device. For example, the applying of a mixture of the organometallic compound and a solvent onto a selected substrate may be a process selected from spin coating, inkjet printing, gravure printing, roll to roll processing, syringe injection, dip coating, spray coating, relief printing, lithography printing, flexography printing, flow coating, and screen printing.

In an implementation, the applying of a mixture of the organometallic compound and a solvent onto a selected substrate may be implemented by, e.g., at least one selected from spray coating, dip coating, spin coating, and flow coating.

The removing of part of the solvent from the mixture applied onto the selected substrate may be implemented by, e.g., to a thermal process.

As used herein, examples of the unsubstituted $C_1$-$C_{60}$ alkyl group (or a $C_1$-$C_{60}$ alkyl group) may be linear or branched $C_1$-$C_{60}$ alkyl groups, including a methyl group, an ethyl group, a propyl group, an isobutyl group, a sec-butyl group, a pentyl group, an iso-amyl group, and a hexyl group. The substituted $C_1$-$C_{60}$ alkyl group refers to a $C_1$-$C_{60}$ alkyl group of which at least one hydrogen atom is substituted with one selected from:

a deuterium atom, —F, —Cl, —Br, —I, —CN, a hydroxyl group, —$NO_2$, an amino group, an amidino group, a hydrazine group, a hydrazone group, a carboxylic acid group or a salt thereof, a sulfonic acid group or a salt thereof, a phosphoric acid group or a salt thereof, a tri($C_6$-$C_{60}$ aryl) silyl group, a $C_1$-$C_{60}$ alkyl group, a $C_1$-$C_{60}$ alkoxy group, a $C_2$-$C_{60}$ alkenyl group, and a $C_2$-$C_{60}$ alkynyl group;

a $C_1$-$C_{60}$ alkyl group, a $C_1$-$C_{60}$ alkoxy group, a $C_2$-$C_{60}$ alkenyl group, and a $C_2$-$C_{60}$ alkynyl group, each substituted with at least one of a deuterium atom, —F, —Cl, —Br, —I, —CN, a hydroxyl group, —$NO_2$, an amino group, an amidino group, a hydrazine group, a hydrazone group, a carboxylic acid group or a salt thereof, a sulfonic acid group or a salt thereof, and a phosphoric acid group or a salt thereof;

a $C_3$-$C_{30}$ cycloalkyl group, a $C_3$-$C_{30}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group; and a $C_3$-$C_{30}$ cycloalkyl group, a $C_3$-$C_{30}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, each substituted with at least one of a deuterium atom, —F, —Cl, —Br, —I, —CN, a hydroxyl group, —$NO_2$, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group.

As used herein, the unsubstituted $C_1$-$C_{60}$ alkoxy group (or a $C_1$-$C_{60}$ alkoxy group) may be a group represented by —OA, wherein A is an unsubstituted $C_1$-$C_{60}$ alkyl group as described above. Examples of the unsubstituted $C_1$-$C_{60}$ alkoxy group may include a methoxy group, an ethoxy group, and an isopropyloxy group. At least one hydrogen atom in the alkoxy group may be substituted with those substituents described above in conjunction with the substituted $C_1$-$C_{60}$ alkyl group.

As used herein, the unsubstituted $C_2$-$C_{60}$ alkenyl group (or a $C_2$-$C_{60}$ alkenyl group) is a $C_2$-$C_{60}$ alkyl group having at least one carbon-carbon double bond in the center or at a terminal thereof. Examples of the alkenyl group are an ethenyl group, a propenyl group, a butenyl group, and the like. At least one hydrogen atom in the unsubstituted $C_2$-$C_{60}$ alkenyl group may be substituted with those substituents described above in conjunction with the substituted $C_1$-$C_{60}$ alkyl group.

As used herein, the unsubstituted $C_2$-$C_{60}$ alkynyl group (or a $C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group (or a $C_2$-$C_{60}$ alkynyl group) may include an ethenyl group, a propynyl group, and the like. At least one hydrogen atom in the alkenyl group may be substituted with those substituents described above in conjunction with the substituted $C_1$-$C_{60}$ alkyl group.

As used herein, the unsubstituted $C_3$-$C_{30}$ cycloalkyl group indicates a cyclic, monovalent C3-C30 saturated hydrocarbon group. Non-limiting examples of the unsubstituted $C_3$-$C_{30}$ cycloalkyl group may include cyclopropyl, cyclobutyl, cyclopentyl, cyclohexyl, and cyclooctyl. At least one hydrogen atom in the cycloalkyl group may be substituted with those substituents described above in conjunction with the substituted $C_1$-$C_{60}$ alkyl group.

As used herein, the unsubstituted $C_3$-$C_{30}$ cycloalkenyl group indicates a nonaromatic, cyclic unsaturated hydrocarbon group with at least one carbon-carbon double bond. Examples of the unsubstituted $C_3$-$C_{30}$ cycloalkenyl group may include cyclopropenyl, cyclobutenyl, cyclopentenyl, cyclohexcenyl, cycloheptenyl, 1,3-cyclohexadienyl, 1,4-cyclohexadienyl, 2,4-cycloheptadienyl, and 1,5-cyclooctadienyl. At least one hydrogen atom in the cyclo alkenyl group may be substituted with those substituents described above in conjunction with the substituted $C_1$-$C_{60}$ alkyl group.

As used herein, the unsubstituted $C_6$-$C_{60}$ aryl group is a monovalent group having a carbocyclic aromatic system having 6 to 60 carbon atoms including at least one aromatic ring. The unsubstituted $C_6$-$C_{60}$ arylene group is a divalent group or polyvalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with those substituents described above in conjunction with the $C_1$-$C_{60}$ alkyl group.

Examples of the substituted or unsubstituted $C_6$-$C_{60}$ aryl group may include a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be easily understood based on those of the unsubstituted $C_6$-$C_{60}$ aryl group and the substituted $C_1$-$C_{30}$ alkyl group described above. Examples of the substituted or unsubstituted $C_6$-$C_{60}$ arylene group may be easily understood based on those examples of the substituted or unsubstituted $C_6$-$C_{60}$ aryl group described above.

As used herein, the unsubstituted $C_2$-$C_{60}$ heteroaryl group is a monovalent group having at least one aromatic ring having at least one of the heteroatoms selected from the group consisting of N, O, P, and S as a ring-forming atom. The unsubstituted $C_2$-$C_{60}$ heteroarylene group is a divalent group or polyvalent group having at least one aromatic ring having at least one of the heteroatoms selected from the group consisting of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the substituted or unsubstituted $C_2$-$C_{60}$ heteroarylene group may be easily understood based on those examples of the substituted or unsubstituted $C_2$-$C_{60}$ arylene group described above.

The substituted or unsubstituted $C_6$-$C_{60}$ aryloxy group indicates —$OA_2$ (where $A_2$ is a substituted or unsubstituted $C_6$-$C_{60}$ aryl group described above). The substituted or unsubstituted $C_6$-$C_{60}$ arylthiol group indicates —$SA_3$ (where $A_3$ is a substituted or unsubstituted $C_6$-$C_{60}$ aryl group described above).

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLES

Synthesis Example 1

Synthesis of Compound 1

3.0 g (0.4 mmol) of FIrpicOH, 52 mg (0.2 mmol) of 1,4-bis(bromomethyl)benzene, and 489 mg (1.5 mmol) of $CsCO_3$ were added to 50 mL of acetone to obtain a reaction mixture, which was then refluxed for about 7 hours. After the reaction product was cooled down to room temperature, the solvent was removed by evaporation in a reduced pressure, and the residue was dissolved in methylene chloride. A resulting organic phase was washed with water and dried using $Na_2SO_4$, followed by evaporation of the solvent to obtain a crude product, which was then purified by silica gel column chromatography using methylene chloride, ethyl acetate, and methanol in a volume ratio of about 10:10:0.2 as eluents, followed by recrystallization using methylene chloride and hexane in a volume ratio of 1:20 to remove the remaining impurities. The recrystallized product was filtered through a Buchner funnel, followed by washing several times with hexane and ethyl ether to obtain 95 mg of a target product (Yield: 31%).

$^1$H NMR (300 MHz, a $CDCl_3$) δ (ppm) 8.58 (d, 4 Hz, 2H), 8.34-8.24 (m, 6H), 8.11-7.90 (m, 6H), 7.74-7.51 (m, 8H), 7.34-7.32 (m, 4H), 6.82 (q, 3 Hz, 4H). 5.67 (d, 4 Hz, 2H). 5.45 (d, 4 Hz, 2H). 5.23 (s, 4H)

Synthesis Example 2

Synthesis of Compound 2

A mixture of 67 mg (0.2 mmol) of 4,4'-bis(bromomethyl)biphenyl, 0.3 g (0.4 mmol) of FIrpicOH, and $Cs_2CO_3$ was reacted at about 70° C. in dimethylformamide (DMF) solvent. After the reaction product was cooled down to room temperature, the solvent was removed by evaporation in a reduced pressure, and the residue was dissolved in methylene chloride. A resulting organic phase was washed with water and dried using $Na_2SO_4$, followed by evaporation of the solvent to obtain a crude product, which was then purified by silica gel column chromatography using methylene chloride and hexane as eluents, followed by further recrystallization using methylene chloride and hexane to obtain 0.089 g of a white solid product (Yield: 28%).

$^1$H NMR (300 MHz, a $CDCl_3$): δ (ppm) 8.60 (d, 4 Hz, 2H), 8.30-8.22 (m, 4H), 8.07-8.02 (m, 4H), 7.94 (d, 6 Hz, 2H), 7.74-7.51 (m, 8H), 7.34-7.32 (m, 6H), 6.82 (q, 3 Hz, 4H). 5.67 (d, 4 Hz, 2H). 5.45 (d, 4 Hz, 2H). 5.21 9s, 8H)

Synthesis Example 3

Synthesis of Compound 3

A mixture of 88 mg (0.2 mmol) of 1,3,5-tris(bromomethyl)-2,4,6-triethylbenzene, 0.3 g (0.4 mmol) of FIrpicOH, and $Cs_2CO_3$ was reacted at about 70° C. in dimethylformamide (DMF) solvent. After the reaction product was cooled down to room temperature, the solvent was removed by evaporation in a reduced pressure, and the residue was dissolved in methylene chloride. A resulting organic phase was washed with water and dried using $Na_2SO_4$, followed by evaporation of the solvent to obtain a crude product, which was then purified by silica gel column chromatography using methylene chloride and hexane as eluents, followed by further recrystallization using methylene chloride and hexane to obtain 0.117 g of a white solid product (Yield: 25%).

$^1$H NMR (300 MHz, a $CDCl_3$): δ (ppm) 8.55 (s, 3H), 8.29-8.01 (m, 14H), 7.69-7.34 (m, 16H), 6.84-6.73 (m, 6H), 5.67 (d, 4 Hz, 3H). 5.43 (d, 4 Hz, 3H). 5.24 (s, 6H), 2.73 (m, 6H), 1.09 (t, 6 Hz, 9H)

Evaluation Example 1

Evaluation of Emission Characteristics of Compounds 1 to 3

Photoluminescence (PL) spectra of Compounds 1 to 3 of Synthesis Examples 1 to 3 were measured to evaluate emission characteristics of Compounds 1 to 3. A PL spectrum of FIrpic as a Comparative Example was measured.

Compounds 1 to 3 in Solution

Compounds 1 to 3 and FIrpic were diluted in toluene to a concentration of about 10 mM. The PL spectrum of each compound in solution was measured using an ISC PC1 spectrofluorometer equipped with a Xenon lamp. The results are shown in FIG. 2.

Compounds 1 to 3 in Film

Sample films of Compounds 1 to 3 and FIrpic, each in about 0.02 mM, were prepared. The PL spectrum of each compound in film was measured using an ISC PC1 spectrofluorometer equipped with a Xenon lamp. The results are shown in FIG. 3.

Figure 2:
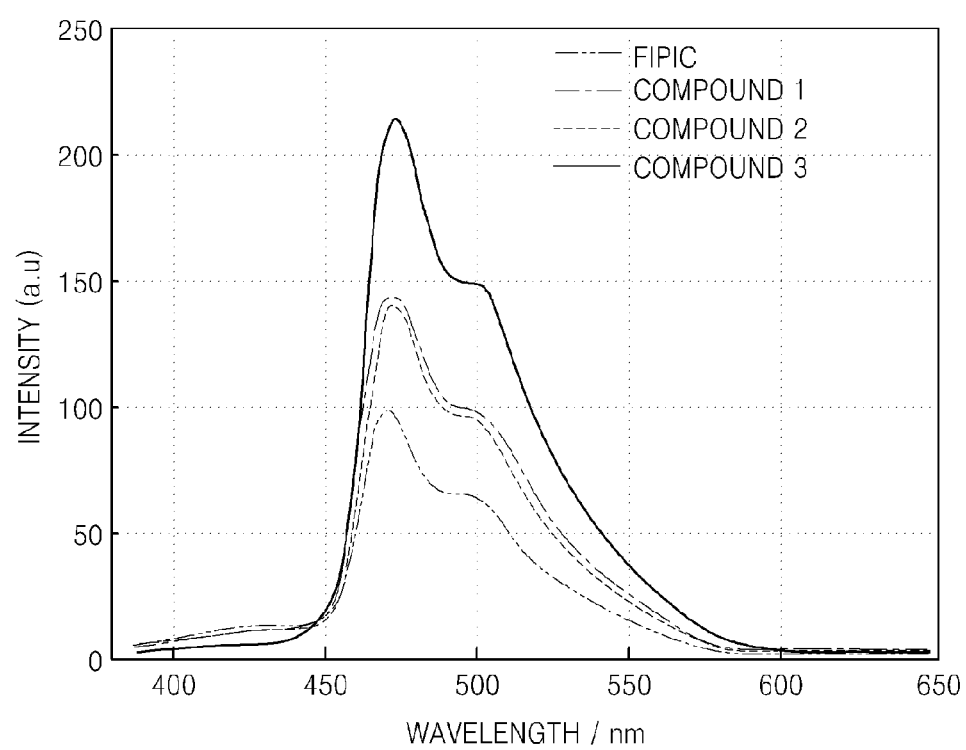
FIG. 2 illustrates photoluminescence (PL) spectra of Compounds 1 to 3 of Synthesis Examples 1 to 3, each in solution.
Figure 3:
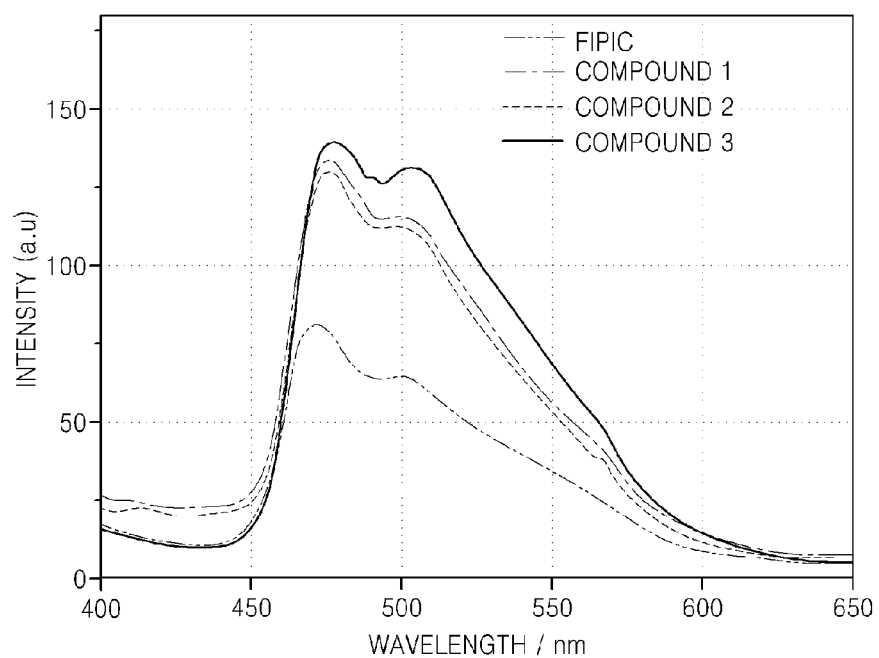
FIG. 3 illustrates PL spectra of Compounds 1 to 3 of Synthesis Examples 1 to 3, each in film.

Referring to FIGS. 2 and 3, Compounds 1 to 3 were found to have better PL characteristics, both in solution and film, compared to FIrpic.

Example 1

To manufacture an anode, a corning 15 Ω/$cm^2$ (120 Å) ITO glass substrate was cut to a size of 50 mm×50 mm×0.7 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

PEDOT and PSS (poly(3,4-ethylenedioxythiophene) (PEDOT) and poly(4-styrenesulfonate) (PSS) were spin-coated on the ITO, and thermally treated at about 65° C. to form a hole transport/injection layer having a thickness of about 45 nm. A mixture of poly(n-vinylcarbazole) (PVK, Mw of 1,100,000), 2-(4-biphenylyl)-5-(4-tert-butylphenyl)-1,3,4-oxadiazole (PBD), and Compound 3 in a weight ratio of 10:3:4 was spin-coated on the hole transport/inject layer, and thermally treated at about 120° C. to form an EML having a thickness of about 30 nm. Balq was deposited on the EML to form an ETL having a thickness of about 30 nm, and then LiF was deposited on the ETL to form an EIL having a thickness of about 1 nm. Then, Al was deposited on the EIL to form a second electrode (cathode) having a thickness of about 100 nm, thereby completing the manufacture of an organic light-emitting device.

Comparative Example 1

An organic light-emitting device was manufactured in the same manner as in Example 1, except that Compound A, instead of Compound 1, was used to form the EML.

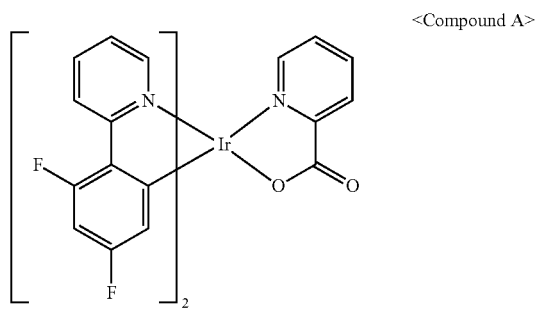

<Compound A>

TABLE 1

| | Dopant | Efficiency (cd/A at 10 mA/$m^2$) | Color coordinates |
|---|---|---|---|
| Example 1 | Compound 3 | 2.81 | (0.20, 0.42) |
| Comparative Example 1 | Compound A | 2.65 | (0.22, 0.43) |

Referring to Table 1, the organic light-emitting device of Example 1 was found to be better in efficiency and color purity, compared to that of Comparative Example 1.

As described above, according to the one or more of the above embodiments, a high-quality organic light-emitting device with high efficiency may be manufactured using an organometallic compound of Formula 1, above. An organic light-emitting device may be manufactured through a solution process using the organometallic compound of Formula 1 above.

The embodiments may provide an organometallic compound, and a high-quality organic light-emitting device manufactured using a solution process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:
1. An organometallic compound represented by Formula 1, below:

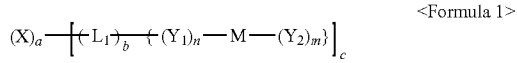

<Formula 1> wherein, in Formula 1,

X is selected from a substituted or unsubstituted $C_4$-$C_{20}$ alicyclic group, a substituted or unsubstituted $C_2$-$C_{20}$ heteroalicyclic group, a substituted or unsubstituted $C_6$-$C_{20}$ aromatic group, or a substituted or unsubstituted $C_2$-$C_{20}$ heteroaromatic group;

a is an integer of 1 to 5, wherein, when a is 2 or greater, X are identical to or different from each other;

M is a transition metal having an atomic weight of 40 or greater;

$Y_1$ is a first ligand selected from a monodentate organic ligand, a bidentate organic ligand, a tridentate organic ligand, or a tetradentate organic ligand;

n is an integer of 1 to 4;

$Y_2$ is a second ligand represented by Formula 2, below;

m is 2;

c is an integer of 2 to 5, and moieties represented by

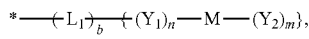

in which * is a binding site to X, are identical to or different from each other, and when c is 2, M are identical to each other;

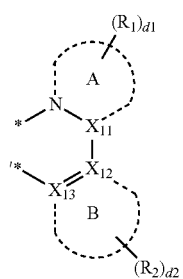

<Formula 2> wherein, in Formula 2, $X_{11}$ to $X_{13}$ are each independently a carbon atom (C) or a nitrogen atom (N);

ring A is a $C_2$-$C_{60}$ heteroaromatic group including at least one nitrogen atom as a ring member;

ring B is selected from a $C_4$-$C_{20}$ alicyclic group, a $C_2$-$C_{20}$ heteroalicyclic group, a $C_6$-$C_{20}$ aromatic group, or a $C_2$-$C_{20}$ heteroaromatic group;

$R_1$ and $R_2$ are each independently selected from a hydrogen atom, a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —C(=O)($Q_3$), and —Si($Q_4$)($Q_5$)($Q_6$), in which $Q_3$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group;

d1 is an integer of 1 to 8, wherein, when d1 is 2 or greater, $R_1$ are identical to or different from each other;

d2 is an integer of 1 to 8, wherein, when d2 is 2 or greater, $R_2$ are identical to or different from each other; and

* and *' in Formula 2 indicate binding sites to M, wherein, in Formula 1, the moiety represented by $(L_1)_b$ is represented by Formula 3, below,

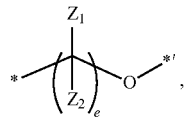

<Formula 3> and wherein, in Formula 3,

* is a binding site to X;

*' is a binding site to $Y_1$ or $Y_2$;

$Z_1$ and $Z_2$ are each independently selected from a hydrogen atom, a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkoxy group, a phenyl group, a naphthyl group, an anthryl group, a dimethylfluorenyl group, a phenylcarbazolyl group, a pyridinyl group, a pyrimidinyl group, a pyrazinyl group, and a triazinyl group; and e is an integer of 1 to 3.

2. The organometallic compound as claimed in claim 1, wherein X is selected from:

an unsubstituted cyclopropane, an unsubstituted cyclobutane, an unsubstituted cyclopentane, an unsubstituted cyclohexane, an unsubstituted cycloheptane, an unsubstituted cyclooctane, an unsubstituted cyclopentene, an unsubstituted cyclopentadiene, an unsubstituted cyclohexadiene, an unsubstituted cycloheptadiene, an unsubstituted bicyclo-heptane, an unsubstituted bicyclo-octane, an unsubstituted benzene, an unsubstituted pentalene, an unsubstituted indene, an unsubstituted naphthalene, an unsubstituted azulene, an unsubstituted heptalene, an unsubstituted indacene, an unsubstituted acenaphthylene, an unsubstituted fluorene, an unsubstituted spiro-fluorene, an unsubstituted phenalene, an unsubstituted phenanthrene, an unsubstituted anthracene, an unsubstituted fluoranthene, an unsubstituted triphenylene, an unsubstituted pyrene, and an unsubstituted chrysene; and a cyclopropane, a cyclobutane, a cyclopentane, a cyclohexane, a cycloheptane, a cyclooctane, a cyclopentane, a cyclopentadiene, a cyclohexadiene, a cycloheptadiene, a bicyclo-heptane, a bicyclo-octane, a benzene, a pentalene, an indene, a naphthalene, an azulene, a heptalene, an indacene, an acenaphthylene, a fluorene, a spiro-fluorene, a phenalene, a phenanthrene, an anthracene, a fluoranthene, a triphenylene, a pyrene, and a chrysene, each substituted with at least one selected from a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one halogen atom, a $C_2$-$C_{60}$ alkenyl group, a $C_2$-$C_{60}$ alkynyl group, a $C_1$-$C_{60}$ alkoxy group, a $C_3$-$C_{30}$ cycloalkyl group, a $C_3$-$C_{30}$ cycloalkenyl group, a $C_3$-$C_{30}$ heterocycloalkyl group, a $C_3$-$C_{30}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and —Si($Q_{13}$)($Q_{14}$)($Q_{15}$), in which $Q_{13}$ to $Q_{15}$ are each independently, a hydrogen atom, a $C_1$-$C_{10}$ alkyl group, a $C_6$-$C_{20}$ aryl group, or a $C_2$-$C_{20}$ heteroaryl group.

3. The organometallic compound as claimed in claim 1, wherein X is selected from:
an unsubstituted benzene, an unsubstituted naphthalene, and an unsubstituted anthracene; and
a benzene, a naphthalene, and an anthracene, each substituted with at least one selected from
a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;
a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group;
a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxy group, a cyano group, a nitro group, and an amino group;
a phenyl group, a naphthyl group, an anthryl group, a carbazolyl group, a fluorenyl group, a pyridinyl group, a pyrimidinyl group, a pyrazinyl group, and a triazinyl group; and
a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group , a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

4. The organometallic compound as claimed in claim 1, wherein a is 1 or 2.

5. The organometallic compound as claimed in claim 1, wherein X is a phenylene group, and a is 1 or 2.

6. The organometallic compound as claimed in claim 1, wherein $L_1$ is bound to $Y_1$ and X.

7. The organometallic compound as claimed in claim 1, wherein M is selected from iridium (Ir), platinum (Pt), osmium (Os), and ruthenium (Ru).

8. The organometallic compound as claimed in claim 1, wherein the first ligand is at least one of the groups represented by Formulae 4 to 12, below:

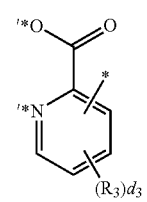

<Formula 4>

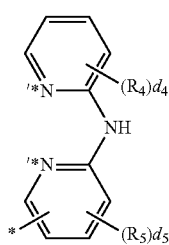

<Formula 5>

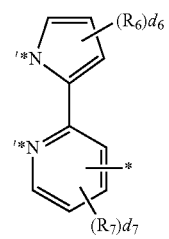

<Formula 6>

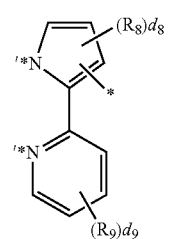

<Formula 7>

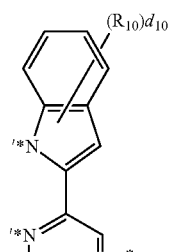

<Formula 8>

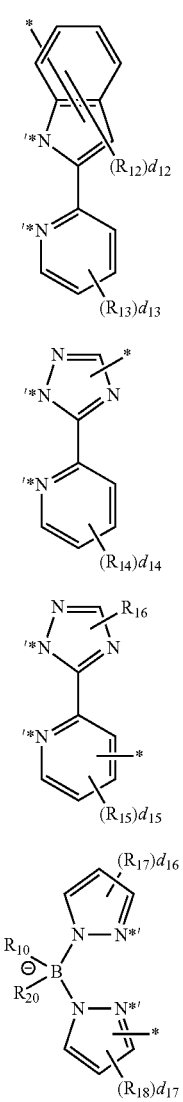

<Formula 9>

<Formula 10>

<Formula 11>

<Formula 12> wherein, in Formulae 4 to 12,
* is a binding site to $L_1$;
*' is a binding site to M;
$R_3$ to $R_{20}$ are each independently selected from a hydrogen atom, a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_3$-$C_{30}$ heterocycloalkyl group, a substituted or unsubstituted $C_3$-$C_{30}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group —C(=O)($Q_3$), and —Si($Q_4$)($Q_5$)($Q_6$), in which $Q_3$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group; and $d_3$ to $d_{17}$ are each independently an integer of 1 to 3.

9. The organometallic compound as claimed in claim 1, wherein, in Formula 2, the ring A is pyridine, and the ring B is benzene.

10. The organometallic compound as claimed in claim 1, wherein, in Formula 2, $R_1$ and $R_2$ are each independently selected from:
a hydrogen atom, a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;
an unsubstituted methyl group, an unsubstituted ethyl group, an unsubstituted n-propyl group, an unsubstituted i-propyl group, an unsubstituted n-butyl group, an unsubstituted i-butyl group, an unsubstituted t-butyl group, an unsubstituted pentyl group, an unsubstituted hexyl group, an unsubstituted heptyl group, an unsubstituted octyl group, an unsubstituted nonyl group, an unsubstituted decyl group, an unsubstituted methoxy group, an unsubstituted ethoxy group, an unsubstituted propoxy group, an unsubstituted butoxy group, and an unsubstituted pentoxy group;
a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxy group, a cyano group, a nitro group, and an amino group;
an unsubstituted phenyl group, an unsubstituted naphthyl group, an unsubstituted anthryl group, an unsubstituted carbazolyl group, an unsubstituted fluorenyl group, an unsubstituted pyridinyl group, an unsubstituted pyrimidinyl group, an unsubstituted pyrazinyl group, and an unsubstituted triazinyl group; and
a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group.

11. The organometallic compound as claimed in claim 1, wherein, in Formula 1, at least one moiety represented by $$*\text{---}(Y_1)_n\text{---}M\text{---}(Y_2)_m\}$$

is a moiety represented by Formula 13 below:

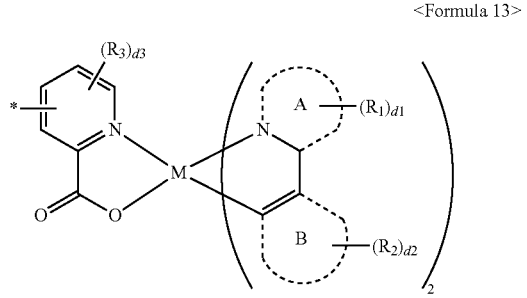

<Formula 13> wherein, in Formula 13,
* is a binding site to $L_1$;
ring A is selected from a pyridine, a pyrimidine, a pyrazine, a triazine, a quinoline, and an isoquinoline;
ring B is selected from a benzene, a naphthalene, a pyrazole, a triazole, a pyridine, a pyrimidine, a pyrazine, a triazine, a quinoline, and an isoquinoline;
$R_1$ to $R_3$ are each independently selected from:
a hydrogen atom, a deuterium atom, a halogen atom, a hydroxy group, a cyano group, a nitro group, an amino group, an amidino group, a hydrazine group, a hydrazone group, a carboxylic acid group or a salt thereof, a sulfonic acid group or a salt thereof and a phosphoric acid group or a salt thereof;
an unsubstituted methyl group, an unsubstituted ethyl group, an unsubstituted n-propyl group, an unsubstituted i-propyl group, an unsubstituted n-butyl group, an unsubstituted i-butyl group, an unsubstituted t-butyl group, an unsubstituted pentyl group, an unsubstituted hexyl group, an unsubstituted heptyl group, an unsubstituted octyl group, an unsubstituted nonyl group, an unsubstituted decyl group, an unsubstituted methoxy group, an unsubstituted ethoxy group, an unsubstituted propoxy group, an unsubstituted butoxy group, and an unsubstituted pentoxy group;
a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group, each substituted with at least one selected from a deuterium atom, —F, a hydroxy group, a cyano group, a nitro group, and an amino group;
an unsubstituted phenyl group, an unsubstituted naphthyl group, an unsubstituted anthryl group, an unsubstituted carbazolyl group, an unsubstituted fluorenyl group, an unsubstituted pyridinyl group, an unsubstituted pyrimidinyl group, an unsubstituted pyrazinyl group, and an unsubstituted triazinyl group; and
a phenyl group, a naphthyl group, an anthryl group, a carbazolyl group, a fluorenyl group, a pyridinyl group, a pyrimidinyl group, a pyrazinyl group, and a triazinyl group, each substituted with at least one selected from a deuterium atom, —F, a hydroxy group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a methyl group, an ethyl group, a n-propyl group, a i-propyl group, a n-butyl group, a i-butyl group, a t-butyl group, a pentyl group, a hexyl group, a heptyl group, an octyl group, a nonyl group, a decyl group, a methoxy group, an ethoxy group, a propoxy group, a butoxy group, and a pentoxy group; and
d1 to d3 are each independently an integer of 1 to 3.

12. The organometallic compound as claimed in claim 1, wherein c is 2 or 3.

13. The organometallic compound as claimed in claim 1, wherein the organometallic compound represented by Formula 1 is one of Compounds 1 to 3 below:

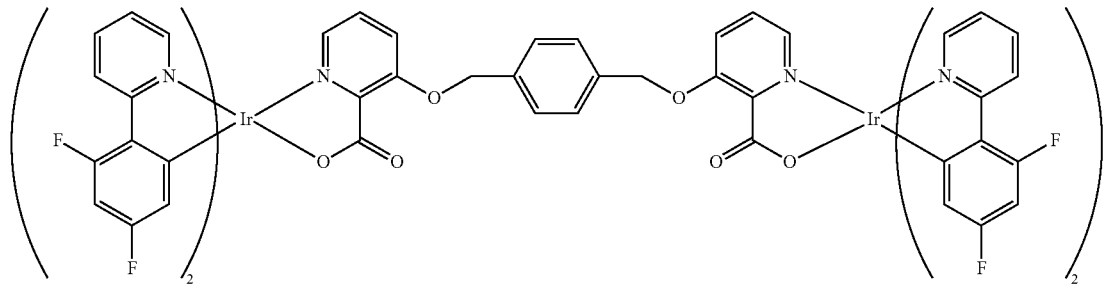

<Compound 1>

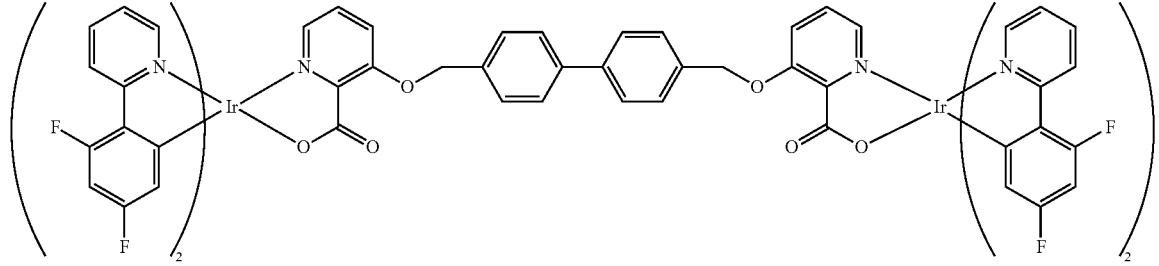

<Compound 2>

-continued

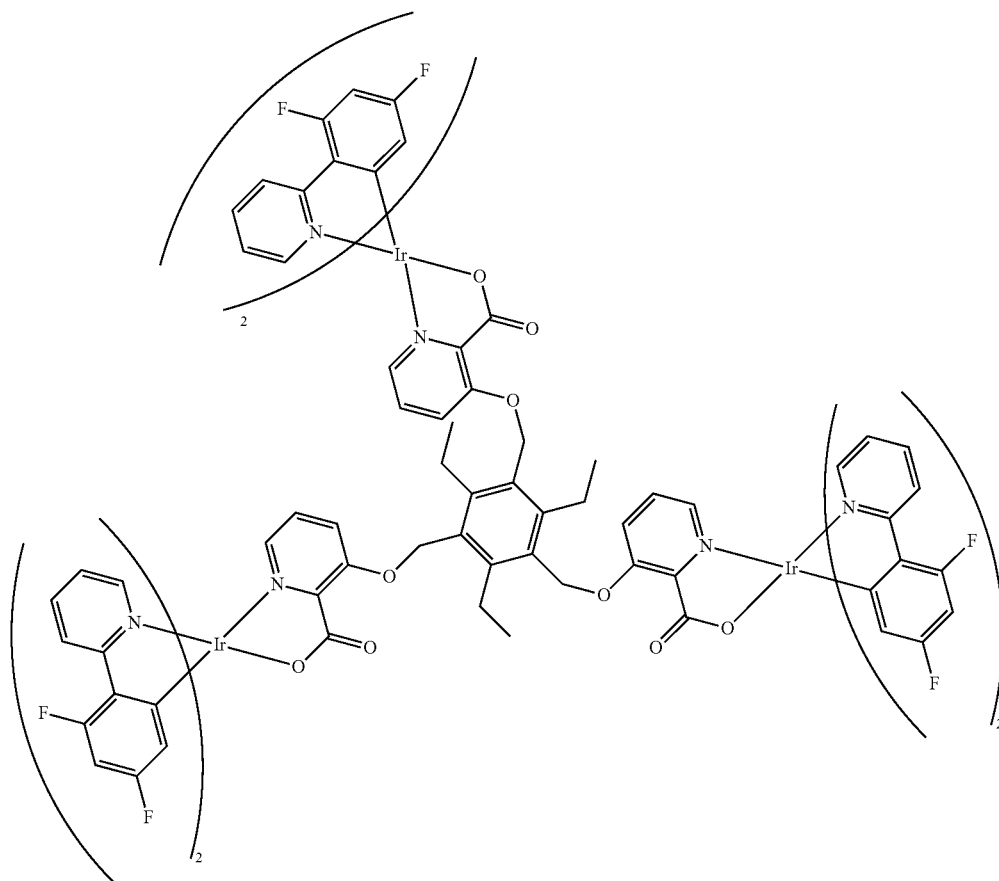

<Compound 3>

14. An organic light-emitting device, comprising:
a substrate;
a first electrode;
a second electrode disposed opposite to the first electrode; and
an organic layer disposed between the first electrode and the second electrode and including an emission layer, the organic layer including the organometallic compound as claimed in claim 1.

15. The organic light-emitting device as claimed in claim 14, wherein the organic layer includes:
a hole transport region between the first electrode and the emission layer, the hole transport region including at least one of a hole injection layer, a hole transport layer, a functional layer having a hole injection capability and a hole transport capability, a buffer layer, and an electron blocking layer, and
an electron transport region between the emission layer and the second electrode, the electron transport region including at least one selected from a hole blocking layer, an electron transport layer, and an electron injection layer.

16. The organic light-emitting device as claimed in claim 14, wherein the emission layer includes a host and a phosphorescent dopant, the phosphorescent dopant including the organometallic compound.

17. A method of manufacturing an organic light-emitting device, the method comprising:
forming a first electrode on a substrate;
forming an organic layer on the first electrode such that the organic layer includes an emission layer and the organometallic compound as claimed in claim 1; and
forming a second electrode on the organic layer,
wherein the forming the organic layer includes:
depositing the organometallic compound on a selected substrate; or
applying a mixture of the organometallic compound and a solvent onto a selected substrate, and removing part of the solvent from the mixture applied onto the selected substrate.

* * * * *